United States Patent [19]
Walter

[11] Patent Number: 5,466,152
[45] Date of Patent: Nov. 14, 1995

[54] METHOD FOR CREATING A DENTAL MODEL

[75] Inventor: Jose Walter, Fairfax, Va.

[73] Assignee: Accu Bite Dental Supply Company, Williamston, Mich.

[21] Appl. No.: 144,558

[22] Filed: Nov. 2, 1993

[51] Int. Cl.$^6$ .......................... A61C 11/00; A61C 19/00
[52] U.S. Cl. .................. 433/60; 433/57; 433/74
[58] Field of Search ................ 433/53, 54, 57, 433/74, 39, 60

[56] References Cited

U.S. PATENT DOCUMENTS

| | | | |
|---|---|---|---|
| 3,937,773 | 2/1976 | Huffman | 433/74 |
| 4,021,916 | 5/1977 | Spalten | 433/74 |
| 4,439,151 | 3/1984 | Whelan | 433/74 |
| 4,449,931 | 5/1984 | Saito | 433/74 |
| 4,451,234 | 5/1984 | Oye | 433/54 |
| 4,842,515 | 6/1989 | Zeiser | 433/74 |
| 5,197,874 | 3/1993 | Silva et al. | 433/74 |
| 5,403,185 | 4/1995 | Presswood | 433/74 |

FOREIGN PATENT DOCUMENTS

| | | | |
|---|---|---|---|
| 2835094 | 2/1980 | Germany | 433/60 |

*Primary Examiner*—Cary E. O'Connor
*Attorney, Agent, or Firm*—Robert L. Knechtel

[57] ABSTRACT

A dental articulation apparatus for creating a pinned model of a patient's mandibular and maxillary dental arches. The apparatus permits the simultaneous relation and construction of pinned, segmental models of the maxillary and mandibular dental arches and allows the model, die, and articulation to be accomplished in a single pouring. The articulator includes recessed maxillary and mandibular tray support members each containing a plurality of indexing holes into which indexing pins can be inserted. A negative dental impression is then filled with a casting material, or alternatively, the support members are filled with a casting material, and the support members and negative impression material are then joined together such that the indexing pins protrude through and into the casting material. Once hardened, the casting material can be removed from the articulating device; the positioning pins allow then sectioned portions of the model to be replaced in the exact position that they were before the model was sectioned. Antirotation devices found on each tray support member prevent the model from turning on its pin axis thereby increasing stability and holding the model accurately in place.

20 Claims, 2 Drawing Sheets

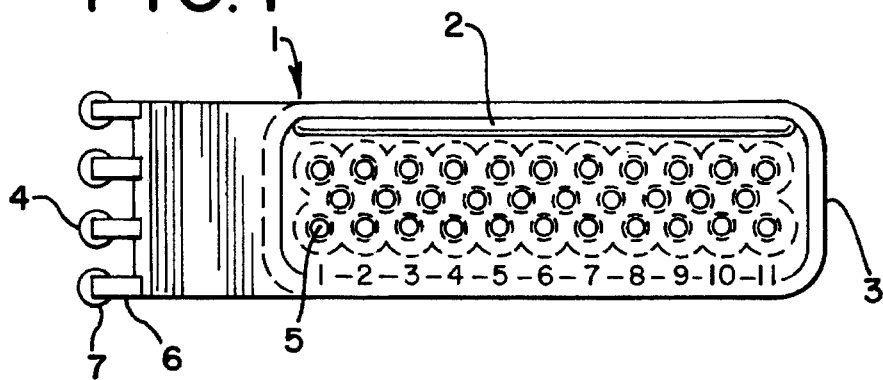
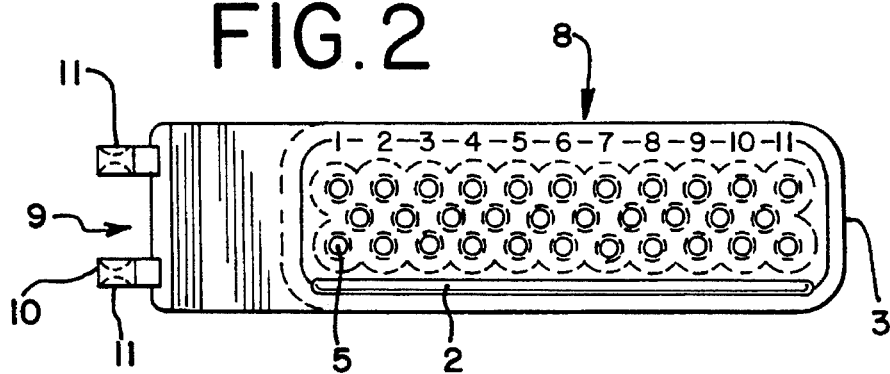
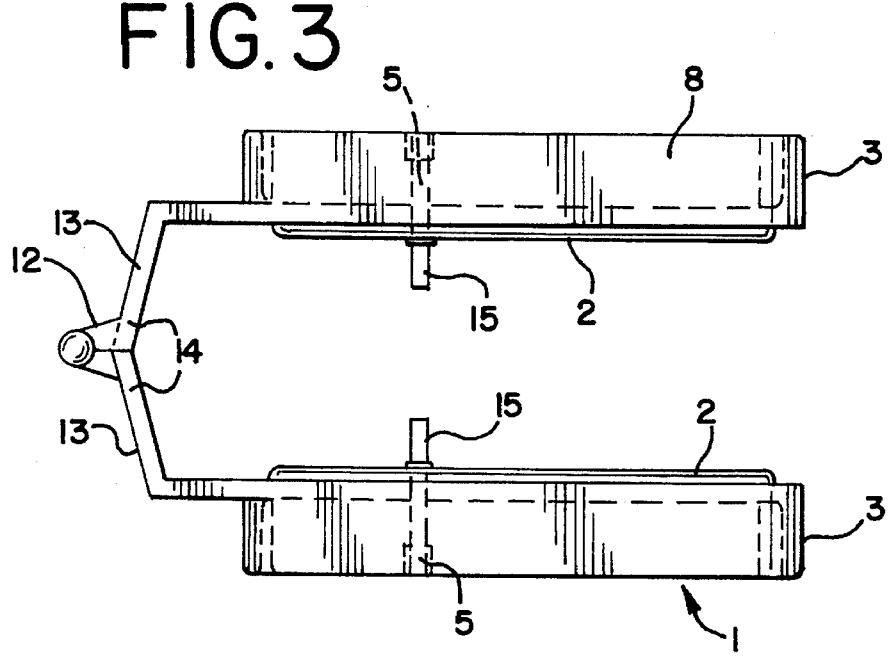

METHOD FOR CREATING A DENTAL MODEL

BACKGROUND OF THE INVENTION

The present invention relates to an apparatus and method for making dental models from which bridges, crowns, and other restorative dental work can be produced.

Restorative work plays a major part in dental care. Restorative measures such as crowns, bridges, and tooth protheses require the use of dental models from which to work. A dental model is typically made by a dentist's first creating a negative impression of the teeth. The negative impression is then filled with a casting material which hardens creating a model of the patient's teeth. In order to work on certain aspects of the model, the casting material must be sawed into usable segments.

Numerous inventions and devices have been devised to facilitate the dental model process. One example of the prior art includes U.S. Pat. No. 4,398,884 to Huffman, which describes an insert, which locks onto the casting material to guide each removal model tooth during insertion into and withdrawal from the dental model. A shortcoming of this art is that it is not possible to relate the maxillary and mandibular dental arches with one another in such a way as to recreate an accurate three-dimensional model showing the arches as they were at the time the mold was made. Another shortcoming of this art is that it requires multiple pours of casting material to create a base and a die.

Another apparatus for creating dental models is disclosed in U.S. Pat. No. 4,708,835, to Kiefer, wherein a base plate containing a plurality of pre-formed holes is fitted with dowel pins in each location where it is desired to make a die removable from a cast dental arch. Two methods of determining which of the pre-formed holes in a base plate are to have dowel pins inserted in them are disclosed. One version requires the use of a transparent datum plate which is positioned over the base plate and fitted with marker pins at desired locations. The data plate is then removed from the carrier plate, flipped over and remounted on the opposite side of the upright of the carrier plate. The base plate is then mounted to the upright of the carrier plate, over the data plate, and dowel pins are inserted into preformed holes in the base plate at those positions occupied by marker pins in the underlying data plate. Both datum plate and base plate with dowel pins inserted are then removed from the carrier plate, and the base plate is again flipped over and remounted to the opposite side of the carrier plate upright over a dental impression containing freshly poured liquid die stone, and pushed downward so the base plate contacts the impression.

In a second version, a transparent base plate having preformed blind holes on one side, and depressions on the opposite side of the plate aligned with the holes, for receiving colored marking ink, is placed over dental impression. Those depressions are locations where dowel pins are desired are then marked with ink and dowel pins inserted in the corresponding blind holes. This is a very complex procedure requiring extensive and unnecessary handling of the mold and casting material.

Another system, disclosed in U.S. Pat. No. 4,371,339 to Zeiser, requires the use of a complicated and expensive orienting apparatus which is has been manufactured to precise tolerances, for holding a dental impression while determining the locations on a prefabricated base plate where holes are subsequently to be made for securing dowel pins which will be molded into a dental arch.

Another method, disclosed in U.S. Pat. No. 4,439,151 to Whelan, describes a method to facilitate the mounting and dismounting of individual teeth by use of a central plastic insert member having projecting elements through the base of the tray to facilitate removal by pushing on said projection portions. The devise also incudes a means to pivot the trays apart to 180 degrees to provide pouring of both tray and impressions. A shortcoming of this art is that a model of only the mandibular or maxillary arch can be made. The model must then be removed from one member of the device and inserted into the second member before work on the model can be accomplished.

SUMMARY OF INVENTION

The problems of multiple pourings, excess handling of materials, use of expensive tooling, inability to relate maxillary and mandibular arches to one another, and time requirements evidenced in the prior art are avoided with the present device.

The present invention relates to an improved apparatus and method for simplifying dental model production while solving the problems not addressed by the prior art.

The invention comprises two tray support members, one relating to the mandibular dental arch and the other to the maxillary dental arch. Each tray support member has opposite ends with one end being a free end and the other end being a hinged end such that when the mandibular and maxillary tray support members are connected together at the hinge they pivot, stopping at a predetermined distance created by a stop means. Each tray support member also has two side walls and a bottom which creates a recessed trough into which casting material may be poured. The bottom portion of the tray support members also contains a plurality of indexing holes into which indexing pins may be inserted. Each tray support member also has an antirotation guide means which prevents segmented portions of a dental model from rotating about a pin's axis should the segment contain only one pin. While the preferred embodiment of invention contains a raised, or convex, antirotation guide means which creates a negative impression in the casting material, a concave antirotation guide means is also contemplated.

The indexing pins contain a base portion and a head portion. The base portion of the indexing pins is fixed in a selected indexing hole and held tight by a pin locking means in the indexing hole. The head portion of the indexing pin is then covered with casting material which is either poured directly into the tray support members or, alternatively, into the negative impression mold. The negative impression mold is then placed over the tray support members and allowed to harden.

Once the casting material is hardened, the hardened casting material may then be removed from the tray support members with the indexing pins being retained in the casting material. The model may be worked on in total or, as more typically occurs, segmented pieces. The segmented pieces may be returned to the support members by placing the segmented portions with their indexing pins back into the same indexing holes from which they were taken. This recreates the dental model as it was when the impression was taken from the patient's mouth. The antirotation guide means assure the precise and accurate alignment of the segmented pieces. While the accompanying figures show the inventive device in such a way as to create a partial dental model, a full mouth dental model device is also contemplated.

The advantages of the inventive device are that it is designed to simultaneously relate and construct pinned, segmental models of the maxillary and mandibular dental arches by relating the arches one to another in a three dimensional relationship that precisely duplicates the relationship that existed at the time the impression of the arches was secured by the dentist.

Simultaneously, this device indexes positioning pins into the model so that the individually prepared teeth can be sectioned from the model to facilitate access to the prepared tooth. The positioning pins consequently allow the section parts of the model to be replaced in the exact position that they were in before the model was sectioned. The sections are held in proper alignment by means of an antirotational device.

OBJECTIVES AND ADVANTAGES

One objective of the inventive device is that it eliminates many steps that previously had to be done to construct pinned, segmented, maxillary and mandibular dental arches. The advantage is that in addition to saving time, the risk of fracturing a dental model is decreased.

Another objective of the inventive device is that it relates mandibular and maxillary dental arch models to one another in a three-dimensional manner. An advantage is that it recreates a patient's mouth for more accurate restorative work.

Another objective of the inventive device is that it produces stable segmental models which heretofore have been a problem in the field. The advantage is that more accurate restorative pieces are produced. Those skilled in the arts will immediately recognize other advantages of the inventive device.

The preferred embodiment of the device is made from transparent high impact poly styrene injection molded plastic; however, other materials may be used.

DRAWINGS

The features and details of the invention are described with greater specificity when referenced to the following drawings:

FIG. 1 is a bottom view of a maxillary tray support member with portions removed;

FIG. 2 is a top plane view of a mandibular tray support member with portions removed;

FIG. 3 is a side view of the maxillary and mandibular tray support members joined via a hinge;

DETAILED DESCRIPTION

Figure 4:
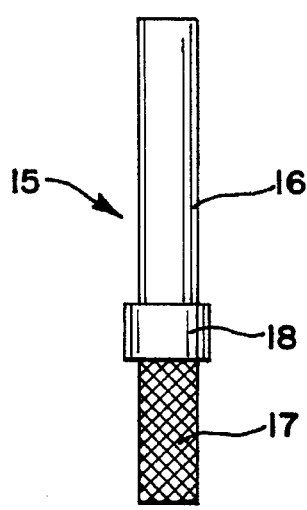
FIG. 4 is a side elevational view of an indexing pin.

FIG. 1 illustrates a maxillary tray support member 1 with an antirotation guide 2 projecting upwardly along one edge of the support member 1 along the length of the support member from its free end 3 to its hinged end 4. Within the body of the tray support member, covering substantially all of the entire plane surface of the support member, are found a plurality of indexing holes 5. At the hinged end 4 of the tray support member 1 are found multiple hinge arms 6 with hinge balls 7.

FIG. 2 illustrates a mandibular tray support member 8 which is a mirror image of the maxillary tray support member 1 shown in FIG. 1 with the exception that at a hinged end 9 are found a plurality of hinged tongues 10 which have sockets 11 contained within. A hinge is formed by snapping the hinge tongues 10 on the mandibular tray 8 between two hinge arms 6 and hinge balls 7 on the opposite maxillary tray support member 1.

The assembled complete device is illustrated in FIG. 3 which is a side view of the maxillary and mandibular support members hinged together at an elbow 12. Uprights 13 connect the maxillary and mandibular tray support members to the hinge arms 6 and hinge tongues 10. At the end of the uprights 13 opposite the trays there is a flat portion 14 which acts as a stop when the two trays are pivoted into the position shown in FIG. 3. Also shown in FIG. 3 are two representative indexing pins 15 placed into indexing holes 5.

FIG. 4 shows the side view of the indexing pin 15 which has a base portion 16, and a head portion 17. The base portion is dimensioned to be closely received in the hole 5. There is a collar 18 which separates the head and base portions and acts as a stop which contacts the tray support members 1 and 8.

Figure 5:
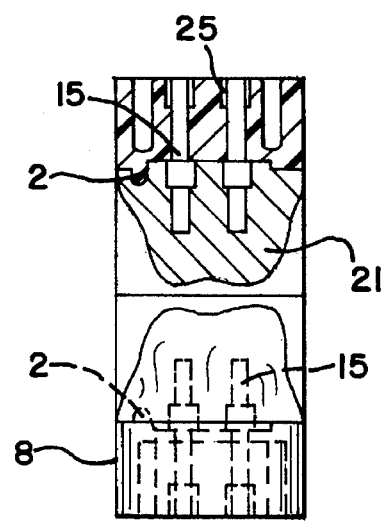
FIG. 5 is an end view partially in cross section of the device from its free end illustrating indexing pins being retained within the casting material.

FIG. 5 shows a view of the inventive device from the free ends 3 wherein the tray support members 1 and 8 have been pivotedly rotated in relationship to one another. A pin locking means 25 secures the indexing pins 15 in place. Representative indexing pins 15 have been placed in the indexing holes 5. Casting material 20 has been poured into place around the antirotation guide 2 and the indexing pins 15.

Figure 6:
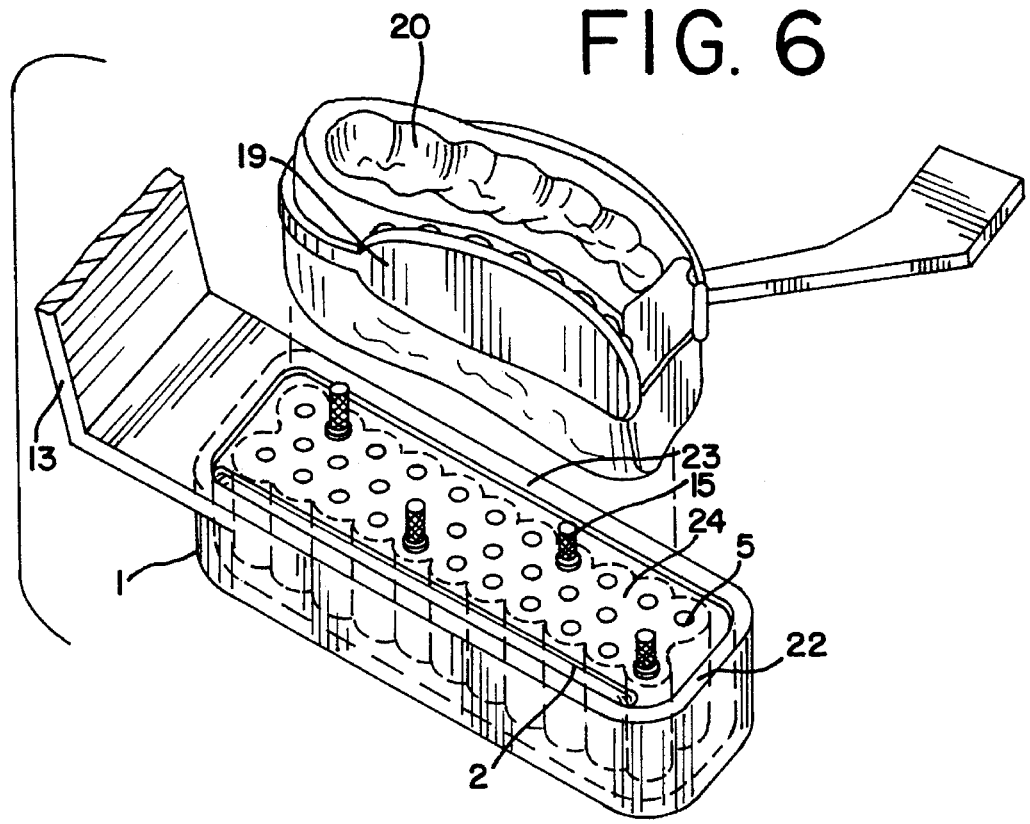
FIG. 6 is a perspective view of a tray support member with indexing pins placed therein and an impression tray in position to be placed onto the tray support member.

FIG. 6 illustrates the tray support member 1 having indexing pins 15 placed into selected indexing holes 5 and an impression tray 19 containing a negative impression mold 20 being placed over the maxillary tray support member 1.

For a typical application, the tray support member 1 has a plurality of indexing pins 15 selectively inserted into indexing holes 5 to the best advantage in working with the dental model. A casting material 18 is poured into the tray support member 1. The casting material 18 is held in the tray support member 1 by raised side walls 23 and raised opposite ends 22. The negative impression material 19 is then fit over the tray support member 1, using the antirotation guide 2 to precisely locate the negative impression material 19 over the preselected indexing hole 5 into which an indexing pin 15 has been placed. The identical procedure is used for preparing the model in the maxillary tray support member 8 of FIG. 2.

Alternatively, the casting material 18 can be poured into the negative impression mold 20. The negative impression material 19 is then fit over the tray support member 1, as described in the remainder above paragraph.

FIG. 3 illustrates the tray support members 1 and 8 assembled and pivotally rotated upon one another wherein the stop 14 creates a predetermined space between the two tray support members 1 and 8 such that the three-dimensional relationship of the patient's mouth can be viewed at precisely the exact location it was when the impression 20 was secured.

The collar 18 limits the amount of pin insertion so that the head portion 17 of the indexing pin 15 rises above the top level of the tray support members 1 and 8 and protrudes into the casting material 18. The antirotation guide 2 allows the negative impression mold 20 to be precisely aligned over the preselected indexing pins 15.

In its application, the invention works to create maxillary and mandibular dental arch models in a single pouring. The models may then be segmented, removed, worked on, and then reset in the precise location from which the segment was taken. The device then allows the maxillary and mandibular arch models to be related to one another in a three-dimensional manner.

What is claimed is:

1. A dental articulator for creating a pinned model of a patent's mandibular and maxillary dental arches from previously made negative impression molds the articulator comprising:

mandibular and maxillary tray support members, each mandibular and maxillary tray support member having raised opposite ends, raised side walls, and a bottom, thereby forming a recessed body into which a casting material may be poured, a hinge means for connecting the two tray support members at one of their ends leaving the other end free to rotate about the hinge means with respect to each other, a plurality of indexing holes passing through the mandibular and maxillary tray support members, indexing pins having head and a base portion which is placed in the indexing holes of the mandibular and maxillary tray support members, the base portion of the pin retained in the tray support member and the head of the pin protruding into the casting material, and positioning means on the maxillary and mandibular tray support members for accurately and precisely placing the impression molds onto the tray support members, whereby the base portion of the indexing pins are inserted into selected indexing holes, casting material is poured into either the maxillary and mandibular tray support members or the negative impression mold, the maxillary and mandibular support tray members are then placed over the negative impression mold, the casting material allowed to harden with the pins therein, such that when the hardened casting material is removed from the tray support members, the indexing pins are retained in the casting material coinciding exactly with the indexing holes on the tray support members.

2. The dental articulator of claim 1 and further comprising stop means for restraining the rotation of the free ends beyond a predetermined point keeping the free ends at least a predetermined set distance apart from each other to simulate the orientation of the patient's dental arches with the patent's mouth closed as occurred when the impression was taken.

3. The dental articulator of claim 2 wherein the stop means comprises flats on the hinge means to restrict pivotal movement beyond a predetermined angle.

4. The dental articulator of claim 1 wherein the hardened casting is cut into segments, each segment having at least one indexing pin, whereby the segments can be removed and reinserted into their precise location on the articulator to recreate the model of the original impression and the relationship of the maxillary and mandibular arches with respect to each other.

5. The dental articulator of claim 1 wherein the indexing holes cover substantially the entire surface of the tray support members.

6. The dental articulator of claim 1 and further comprising a pin locking means disposed in the indexing holes to maintain the pins in a removable locked relationship after being inserted into the indexing holes.

7. The dental articulator of claim 6 wherein the base portion of the pin is greater in length than the head of the pin, the base portion retained by the pin locking means.

8. The dental articulator of claim 1 wherein the positioning means comprises an antirotational guide extending along an edge of the tray support members, the impression mold being accurately positioned with respect to the antirotation guide.

9. The dental articulator of claim 1 wherein the antirotation guide prevents segments containing only one indexing pin from rotating about the pin's axis.

10. The dental articulator of claim 1 wherein the mandibular and maxillary tray support members are U-shaped to accept impression molds of the patient's entire mouth.

11. The articulator of claim 10 and further comprising stop means for retaining the rotation of the ends of the tray support members opposite the hinge means keeping said ends at least a predetermined said distance apart from each other to simulate the orientation of the patient's dental arches with the patient's mouth closed.

12. The articulator of claim 10 wherein the hardened casting is cut into segments, each segment having at least one indexing pin, whereby the segments can be removed and reinserted into their precise location on the articulator to recreate the model of the original impression and the relationship of the maxillary and mandibular arches with respect to each other.

13. The dental articulator of claim 10 wherein the stop means comprises flats on the hinge means to restrict pivotal movement beyond a predetermined angle.

14. The articulator of claim 10 wherein the indexing holes cover substantially the entire top surface of the tray support members.

15. The dental articulator of claim 14 wherein the base portion of the pin is greater in length than the head of the pin, the base portion retained by the pin locking means.

16. The dental articulator of claim 10 and further comprising indexing pin locking means disposed in the indexing holes to maintain the pins in a removable locked relationship after being inserted into the indexing holes.

17. The dental articulator of claim 10 wherein the positioning means comprises an antirotation guide means extending along an edge of the tray support member, the impression mold being accurately positioned with respect to the antirotation guide.

18. The dental articulator of claim 10 wherein the antirotation guide prevents segments containing only one pin from rotating about the pin's axis.

19. The dental articulator of claim 10 wherein the mandibular and maxillary tray support members are U-shaped to accept impression molds of the patient's mouth.

20. A dental articulator for creating a pinned model of a patient's mandibular and maxillary dental arches from previously made negative impression molds, the articulator comprising:

Mandibular and maxillary tray support members, each tray support member having raised opposite ends, raised side walls, a top surface and a bottom surface, thereby forming a recessed body, a hinge means for connecting the two tray support members at one of their ends, the ends opposites the hinge means free to rotate about the hinge means, a plurality of indexing holes passing through the mandibular and maxillary tray support members, indexing pins having head and base portions, the pins being placed through the top surface of each tray support member with the base portion being retained in the tray support member and the head of the pin protruding into the casting material, and positioning means on the top surface of the tray support members for accurately and precisely placing the impression molds onto the tray support members, whereby the base portion of the indexing pins are inserted into selected indexing holes, casting material is poured into either the maxillary and mandibular tray support members or the negative impression mold, the maxillary and mandibular support trays are then placed over the negative impression mold, the casting material allowed to harden with the pins therein, such that when the hardened casting material is removed from the tray support members, the indexing pins are retained in the casting material coinciding exactly with the indexing holes on the tray support members.

* * * * *

UNITED STATES PATENT AND TRADEMARK OFFICE
CERTIFICATE OF CORRECTION

PATENT NO. : 5,466,152

DATED : Nov. 14, 1995

INVENTOR(S) : Jose Walter

It is certified that error appears in the above-identified patent and that said Letters Patent is hereby corrected as shown below:

Title page, item [54] and column 1, lines 1-2, should read --APPARATUS FOR CREATING A DENTAL MODEL--

Signed and Sealed this

Twenty-seventh Day of February, 1996

Attest:

BRUCE LEHMAN

Attesting Officer

Commissioner of Patents and Trademarks